United States Patent
Anderberg et al.

(12) 
(10) Patent No.: US 6,486,482 B1
(45) Date of Patent: Nov. 26, 2002

(54) IRRADIATION EQUIPMENT

(75) Inventors: Bengt Anderberg, Uppsala (SE); Mikael Lindholm, Enköping (SE)

(73) Assignee: Scanditronix Medical AB, Uppsala (SE)

( * ) Notice: Subject to any disclaimer, the term of this patent is extended or adjusted under 35 U.S.C. 154(b) by 0 days.

(21) Appl. No.: 09/462,233

(22) PCT Filed: Jun. 30, 1997

(86) PCT No.: PCT/SE97/01179

§ 371 (c)(1), (2), (4) Date: May 30, 2000

(87) PCT Pub. No.: WO99/00801

PCT Pub. Date: Jan. 7, 1999

(51) Int. Cl.⁷ ............................ G21G 5/00; G21C 11/00
(52) U.S. Cl. ............................. 250/492.3; 250/455.11; 250/496.1; 250/515.1
(58) Field of Search ................... 250/455.11, 492.3, 250/496.1, 498.1, 515.1

(56) References Cited

U.S. PATENT DOCUMENTS

| | | | |
|---|---|---|---|
| 4,075,496 A | 2/1978 | Uehara | 250/492 B |
| 4,201,920 A | 5/1980 | Tronc et al. | 250/492 B |
| 4,252,413 A * | 2/1981 | Nablo | 250/310 |
| 4,281,251 A | 7/1981 | Thompson et al. | 250/398 |
| 4,492,873 A | 1/1985 | Dmitriev et al. | 250/492.3 |
| 5,004,926 A | 4/1991 | Vassenaix et al. | 250/492.3 |

FOREIGN PATENT DOCUMENTS

EP   0 445 964   9/1991

OTHER PUBLICATIONS

Andersson, B., International Search Report, International Application No. PCT/SE97/01179, Apr. 7, 1998, pp. 1–2.

\* cited by examiner

*Primary Examiner*—Jack Berman
*Assistant Examiner*—Kalimah Fernandez
(74) *Attorney, Agent, or Firm*—Jenkens & Gilchrist, P.C.

(57) ABSTRACT

An arrangement and a method for irradiation of products by charged particles. The arrangement comprises a particle acceleration device and a radiation chamber, in which the products are irradiated from at least two sides, by that the particle beam is deflected with a scanning magnet and redeflected with redeflection magnets. The particle beam impinges on the products substantially parallel to the main normals of the surfaces of the products, which normals are positioned substantially perpendicular to the direction that the radiation axis has immediately before the deflection. An absorption means comprising a particle stopper is arranged in the space between the pole pieces of the redeflection magnets. A transport device for double-sided irradiation transports the products, which during transport are fixed to the transport device, through the irradiation arrangement.

21 Claims, 4 Drawing Sheets

IRRADIATION EQUIPMENT

The present invention generally relates to an arrangement for irradiation of products with charged particles.

By existing technology, there are presently three main approaches of sterilising. The first approach is by heating in an autoclave. This method can only be used for heat resistive materials. Since many products are not heat resistive, they are not treatable in an autoclave.

Another approach is to expose the product to poisonous gas. This poisonous gas is normally ethylene oxide, which is poisonous, carcinogenic and explosive. The use of this gas is surrounded by extensive security regulations. Among other things, the products have to be ventilated during a very long time period in order to decrease the rest level of gas in the material to approved levels. The products are packed in a semi-permeable package and ventilating of gas takes place through this layer. Bacterial cultivation is requested before the products are allowed to be delivered. Together, all this results in that a normal treatment time becomes 7–10 days, transports excluded. Rest levels of gas in the material are considered as very dangerous and the tendency is that the allowed limits are continuously lowered.

The third approach is to use ionising radiation. A great advantage with such methods is that they are considered as very safe, and for confirmed absorbed radiation doses above 25 kGy, no bacterial cultivation has to be performed before delivery. Furthermore, the products may be packed before the sterilisation, since the radiation penetrates the package materials. One type of ionising radiation used is gamma radiation from cobalt sources. These radiation sources are generally very strong, in the order of magnitude of 1 MCi, which requires strong radiation shields, e.g. concrete walls with a thickness of 2 m. The penetration ability is very good, but the exposure time is very long, sometimes up to several days.

Another type of ionising radiation is charged particles from accelerators, preferably electrons. They have a more limited penetration depth, but is generally much easier to handle. Known technology uses 10 MeV electrons to achieve a penetration depth in the materials which is large enough. This calls for large accelerators and even in such cases, the radiation shield may consist of up to 2 m of concrete. In order to be able to use such methods, practically and economically, large separate central plants are demanded. Contract sterilising is the normal proceeding for plants of ionising radiation, which means that the sterilising is performed separate from the production, which in turn gives rise to long storage times and transport costs. The investments for such plants are in the order of magnitude of 30–60 million Swedish kronor.

An alternative manner is to irradiate the products with charged particles of a lower energy, preferably electrons, which gives a lower penetration depth. In order to be able to use this method in practice, by use of known technology, which only irradiates the products from one side, the products have to be turned and run another time through the sterilising device to achieve a sufficient penetration depth. This normally gives rise to internal logistic problems and risks for mishandling, unless double arrangements are used after each other.

One way to irradiate an object from different directions is known from INP Novosibirsk (c.f. the U.S. Pat. No. 4,121,086). In this concept, the electron beam from an accelerator is deflected into two alternative beam paths besides the undeflected beam path, which three beam paths in the end impinges on the radiation target in one and the same spot, but from three different directions. The deflection is performed by a deflection magnet and redeflection of the deflected beams is performed by two redeflection magnets. However, this radiation source only operates with three discrete beam paths with individually scanned beam. Such a radiation device is mainly suited for radiation of products with circular cross section, or fluids transported through the irradiation area in circular pipes.

In the U.S. Pat. No. 4,201,920, an irradiation arrangement for irradiation of products from two sides with a scanning electron beam is disclosed. The radiation target is asymmetrically arranged in the area scanned by the electron beam and electrons not impinging directly on the radiation target are deflected to impinge on the back side of the radiation target. The pole pieces of the electromagnet are adapted dependent on the shape and size of the radiation target, to give a homogeneous irradiation. However, this equipment has a number of severe disadvantages.

A first disadvantage is that one has to modify the geometrical shape of the pole pieces for irradiation of products with different shape or size in order to, according to the description, achieve an optimally efficient irradiation. This implies a costly and time consuming pole change when changing the products to be irradiated. If instead the same pole pieces are kept, the patent does not disclose anything about how a control of the scanning could make the use of the beam time more efficient.

Furthermore, the electrons which are redeflected are moving along a longer geometrical path, which means other focusing properties for the redeflected electron beam as compared with the directly impinging electron beam, when they impinge on the products to be irradiated. How such irradiation inhomogenities are to be compensated for is not discussed in the document.

A third disadvantage with the device in the U.S. Pat. No. 4,201,920 arises at irradiation of products which do not continuously occupies the full available radiation sector, e.g. for irradiation of products of an uneven shape or when the products are separated by an interspace. This is the normal case during production of medical disposable products. In these cases, at least a part of the beams will pass the radiation area without being absorbed. These will instead be incident back towards the products and may cause incorrect and inhomogeneous dose distribution. Furthermore, this effect is not equal for the two different sides of the product.

To use an irradiation arrangement efficiently, the products to be irradiated are normally transported in and out from the radiation sector during operation. This is performed by means of any conveying system or assembly line system through the irradiation arrangement. A usual problem is that products are stuck or moving on the conveyor belt. This is particularly true for small, irregular and flabby packages. The most common way of conveying is to let the products lie on a conveyor belt, which passes them into the irradiation arrangement, through the radiation sector and out from the arrangement. The path of the conveyor belt has to be bent in order to be able to efficiently protect for secondary X-ray radiation, i.e. pass through a so-called labyrinth. The risk for that the products are moving at the conveyor belt or are stuck within the irradiation arrangement is large by such technical solutions. The result is varying uncontrolled radiation doses and risk for fire, respectively, since a power of above 6 kW is used. If an internal radiation dose measurement is used, all electronics is rapidly destroyed by the ionising radiation and has to be replaced periodically. If the products, considering the economical efficiency, are packed close together, the risk for overlapping, shadowing and halts increases with an unacceptable quality as the result.

In order to overcome the above described disadvantages and to provide an irradiation arrangement which is simple and small enough for being installed directly in a production line, the present invention presents a solution. The invention provides a device for double-sided irradiation of the products by electrons with a relatively low energy (1–10 MeV), and preferably between 1, 5 and 2, 5 MeV, which penetrates goods with a thickness less than 1 g/cm². The device comprises controllable means, which causes the particle beam to scan over the surface of the product from two sides with controllable focusing properties. The scanned particle beams are preferably incident towards the product in an angle close to 90 degrees and particles, not absorbed by the product or in the vacuum windows surrounding the products, impinge on a particle stopper, supplied for this purpose. The controllable means preferably comprises a focusing lens, a controllable scanning magnet for deflection of the particle beam and two redeflection magnets for bringing the particle beams back to the radiation area for the products. The scanning magnet and the focusing lens are controlled in such a manner that a homogeneous irradiation is achieved over the entire radiation sector from two opposite directions.

A conveyor device has been constructed, which allows the double-sided irradiation at the same time as it flexibly fixes the products during the transport through the irradiation arrangement, whereby the radiation dose to which the products are exposed may be totally controlled by the feeding velocity of the conveyor device.

Owing to that a lower particle energy and a double-sided irradiation is used, the size of the arrangement, including the radiation shield may be made relatively small. Together with the design of the conveyor device, this results in that the arrangement may fit together with a normal production line.

Other advantages and features are described referring to an exemplifying embodiment in the following detailed description and in connection with the associated drawings.

Figure 1:
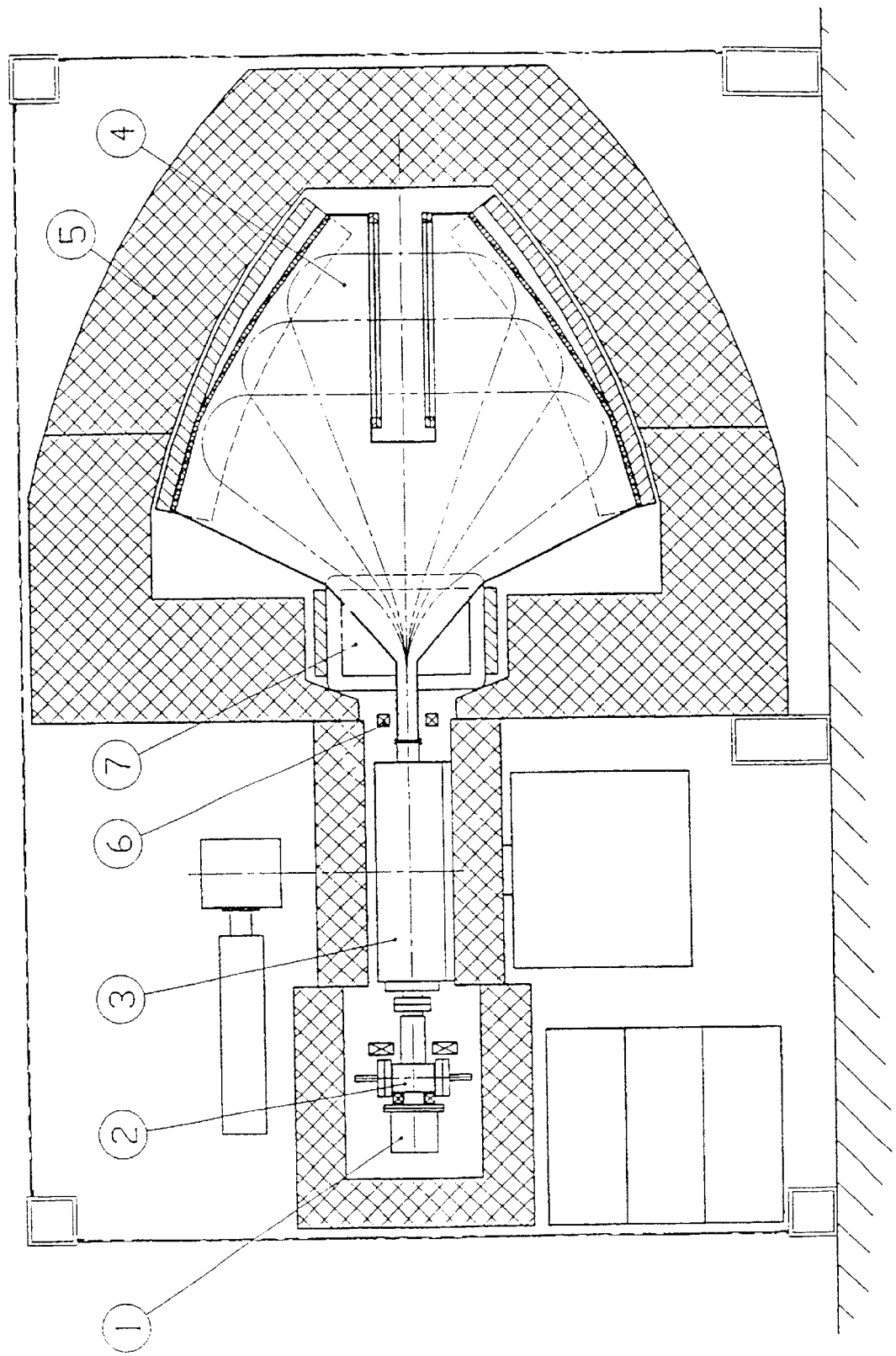
FIG. 1 is a vertical cross section through a sterilising device according to the present invention.

FIG. 1 shows an embodiment of a sterilising device comprising an irradiation arrangement according to the present invention. The irradiation arrangement comprises a particle accelerator. The particle accelerator comprises a particle source 1, a buncher 2 and linear accelerator 3. The particle source 1, in this embodiment an electron gun, which is built in a conventional manner, emits the particles to be used for the irradiation. In this embodiment, the electron gun 1 is of a Pierce type. The buncher 2 pushes the original continuous electron beam together in bunches and introduces the bunches as electron pulses into a linear accelerator 3. Thereby, fewer electrons end up outside any accelerable phase window in the linear accelerator 3, at the same time as the energy dispersion of the electron beam output from the accelerator reduces. In this embodiment, the buncher gives particle pulses of a frequency of 3 GHz. The linear accelerator accelerates the particles by means of electrical fields and sends in the particles towards a radiation chamber 4. In this embodiment, the particles are accelerated to an end energy of 1.5 to 2.5 MeV, and with a particle pulse current in the order of magnitude of 800 mA, which gives an average particle current of 2.4 mA. The pulse lengths are about 5 µs and the pulse repetition frequency is 600 Hz. The particle beam is focussed by a quadropole magnet 6 at the exit of the linear accelerator, before it enters into a scanning magnet 7. The total arrangement comprising particle accelerator and radiation chamber is enclosed by radiation shields 5, consisting of lead, with an approximate thickness of 250 mm.

Figure 2:
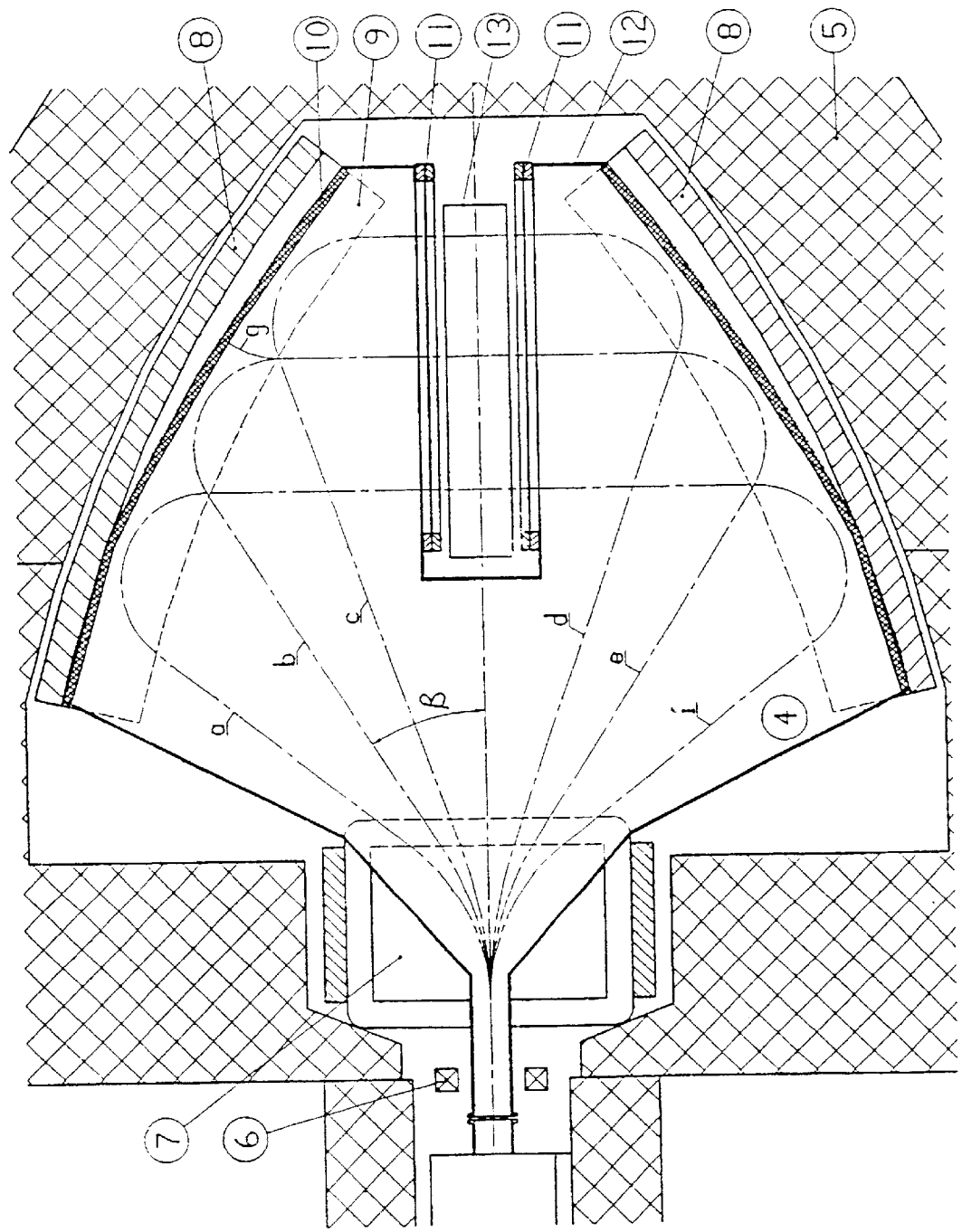
FIG. 2 is an enlargement of a part of the irradiation equipment of the sterilising device shown in FIG. 1.

In FIG. 2, an enlarged drawing of the radiation chamber is shown. When the particle beam leaves the accelerator, it is bent by the scanning magnet 7 in an angle β with respect to the original radiation axis. The angle β may in this embodiment vary between about 15 and 45 degrees, in both positive and negative directions. The scanning magnet is an electromagnet operated by a bipolar current supply, the output current of which may be programmed. The particle beam is incident in a direction of redeflection magnets 8, 9, positioned at each side. The redeflection magnet 8, 9 is in this embodiment a permanent magnet with a particular shape, which is described more in detail here below. When the particle beam enters between the pole pieces 9 of the redeflection magnets, it is bent into a path determined by the magnet flux in the pole gap which is adapted for a deflection angle of β+90°, which implies that the particle beam leaves the field of the redeflection magnet in a path perpendicular to the original radiation axis. The particle beam passes a vacuum window 11, which normally consists of a thin metal foil of titanium or aluminum. In the central area of the radiation chamber 4, hereinafter referred to as the radiation sector 13, the products to be irradiated pass on a conveyor belt 14 (see FIG. 3). The radiation beam will therefore impinge on the products with a radiation angle of essentially 90 degrees with respect of the original radiation axis. Beam optics calculations have been performed to determine the size of the radiation spot. In this embodiment, the radiation spot at the position of the irradiated products is approximately 20 mm. The part of the radiation passing the radiation sector 13 and the two vacuum windows 11 without being absorbed, e.g. as a result of that there are no products in the radiation sector at the moment, continues a rectilinear path until it enters between the pole pieces 9 of the opposite redeflection magnet, is bent and absorbed by a cooled particle stopper 10, preferably made by copper or aluminum. FIG. 2 further shows a radiation chamber boundary 12.

In FIG. 2, six of the innumerable possible particle paths a–f in the radiation chamber are shown. Each particle path is characterised by its exit angle β from the scanning magnet 7. By changing the output current from the current supply of the scanning magnet, the exit angle β may be changed. This exit angle uniquely determines the position where the particle beam enters into the magnet field of the redeflection magnets and is started to be bent. The bending of the particle beam is performed along a circular arch, the radius of which is determined by the mass and velocity of the particle and the strength of the magnetic field. This embodiment is based on a perpendicular irradiation of the products, which gives rise to a demand that the particle beam should leave the influence of the redeflection magnet under a right angle with respect of the original beam axis. If one starts from the position, where the particle beam enters into the magnet field of the redeflection magnet, and the bending radius is known, a position, where the beam has a perpendicular direction, is uniquely defined. This position has to coincide with the position where the particle beam leaves the magnet field, whereby the local appearance of the redeflection magnet uniquely is determined. Since the particle beams enter into the field of the redeflection magnet in different angles at different positions, the design of each small part of the redeflection magnet is determined by the demand of the perpendicular irradiation angle. A shape of the redeflection magnet 9 may thereby, mainly by pure geometrical considerations, easily be calculated. The same considerations are of course valid for the opposite redeflection magnet, when the angle β is negative.

In the shown embodiment, the geometry of the redeflection magnet has been approximated to a circular arch. The centre of the circle is placed 0.77 cm from the entrance to the scanning magnet as measured along the entering beam and 97.2 cm from the axis of the entering beam. The circle has a radius of 139.8 cm. The angle of irradiation will in this case deviate from 90 degrees by less than 1 degree for all scanning positions.

By changing the output current from the current supply of the scanning magnet, the particle beam may thus irradiate the products 13 perpendicularly at different positions, and by changing the polarity of the current, the products may also be irradiated from the other side. If the current through the scanning magnet has a high positive value, the particle beam is bent by a large angle and follows e.g. the particle path a and impinges on the irradiated product close to its inner, towards the accelerator facing, end. When the current then gradually is reduced, the exit angle from the scanning magnet will decrease, which in turn leads to that the particle beam hits the irradiated product increasingly further out, away from the accelerator. The particle beam c, with a rather small exit angle, impinges on the product at its farther end, and its exit angle is so small that it starts to become disturbed by the mechanical parts of the vacuum enclosure. A particle beam with an exit angle with lower absolute value, is thus not to any real use and forms only radiation losses, why the current supply of the scanning magnet rapidly changes its polarity to give rise to a particle beam d, with corresponding negative exit angle instead. This particle beam irradiates the outer part of the product, but now from the other side. By now gradually, in absolute figures, increase the current through the scanning magnet, a particle beam with a gradually larger negative exit angle is achieved, whereby the beam irradiates the product closer to the accelerator end. In order to return to the original state, it is advantageously to scan back in a similar manner, since one otherwise easily would get problems with rapid current changes in the scanning magnet. The particle beam during a complete scan, thus starts e.g. from the path a, scans over to the path c, then rapidly changes to the path d and scans over to the path f, after which it turns and scans back to the path d, rapidly changes over to path c and scans back to the original path a. In this embodiment, the largest exit angle is approximately 45°, while the angle of the smallest absolute value is approximately 15°.

At the occasions, when the radiation sector is not fully covered by the products to be irradiated, e.g. for irregularly formed products or for interspaces between the products when they are transported past the radiation sector, a part of particle beam will pass the radiation sector 13 and the vacuum windows 11 without being absorbed. This radiation continues in a rectilinear path towards the opposite redeflection magnet 8, 9. When the beam enters between the pole pieces 9 of the redeflection magnet, it is bent into a curved path. Due to the direction of the magnetic field, this curvature will be directed away from the accelerator. Examples of such a path is indicated by g in FIG. 2. These paths will impinge on the particle stopper 10 positioned at either side, where the particles are absorbed and the heat generation thereby occurring is collected by the cooling medium of the particle stopper. In this way it is avoided that the radiation which is not absorbed by the products will destroy the irradiation arrangement from the inside or will cause incorrect dose distribution. In the present embodiment, the particle stopper is made of aluminium or copper and the cooling medium in the particle stopper is circulating water. Aluminium has the advantage to have a low cross section for X-ray emission, while copper has the advantage of conducting the heat very efficiently. Both materials may advantageously be used in vacuum applications.

Each beam leaving the particle accelerator 1–3 has a certain emittance and energy dispersion. In the shown embodiment, the emittance has been assumed to be 5 mm mrad and the energy dispersion ±3%. This means that along the path of the beam, the cross section of the beam will vary slowly. Each element along the path of the beam has its characteristic manner to influence the properties of the particle beam. This means, that if one compares the size of the radiation spot at the radiation sector, with identical settings for the quadropole lens, between two different deflections in the scanning magnet, these will differ. Such a variation may give rise to an inhomogeneous irradiation of the product. To compensate for this effect, the quadropole lens 6 may in this embodiment of the invention be used to change the focusing properties of the particle beam at different deflection angles.

Figure 4:
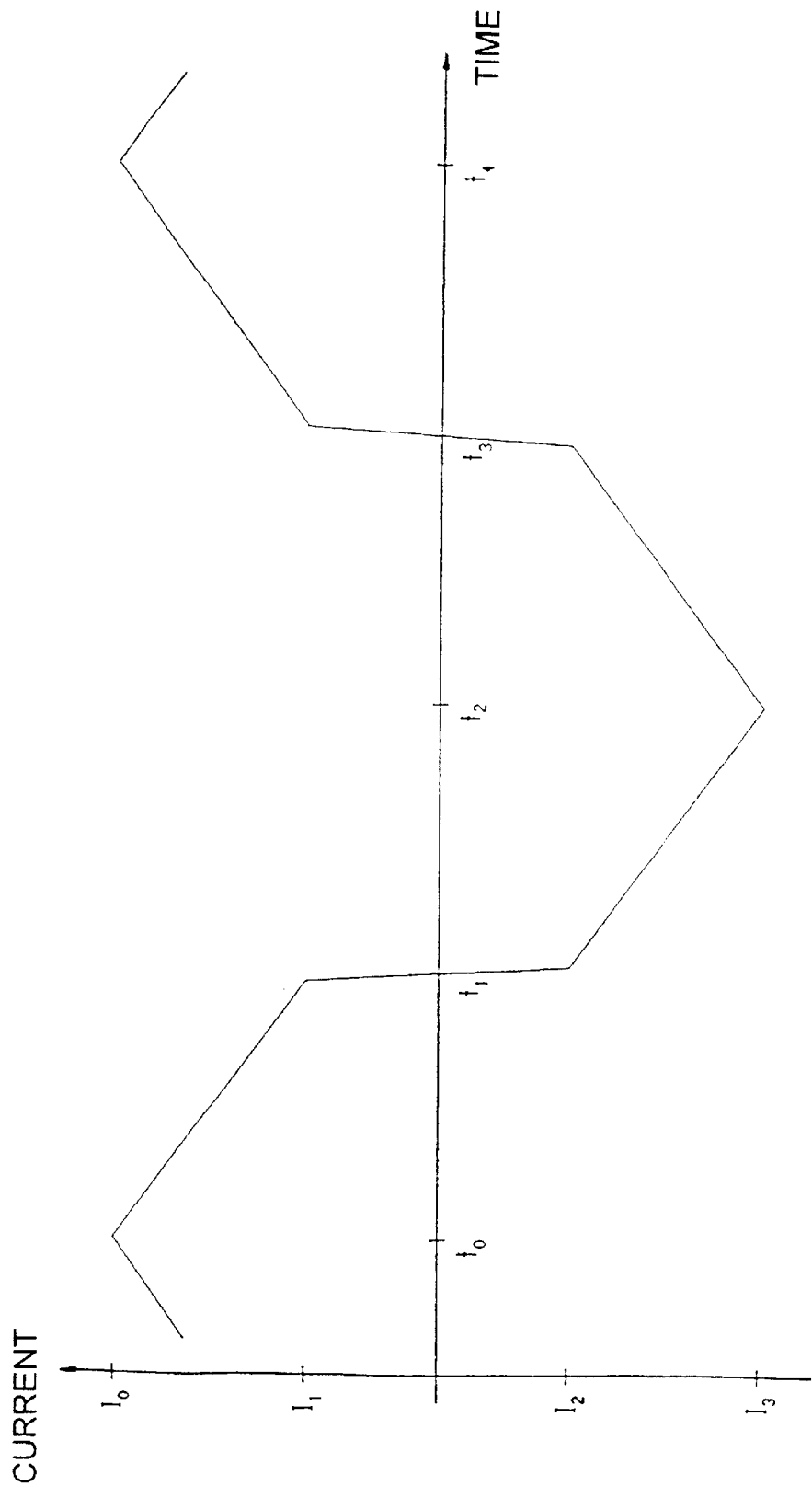
FIG. 4 is a diagram showing a typical behaviour of the variation of current in the scanning magnet during a scanning cycle.

It is important that the products at the conveyor belt are irradiated with an even dose over the entire irradiated area. Since the relation between the current of the scanning magnet and the radiation position on the product generally does not follow a linear relation, the scanning of the current has to be adapted in such a way that the irradiation of the product becomes even. An example of a typical current diagram for a scanning cycle is illustrated in FIG. 4. The scanning starts at the time $t_0$, where the current $I_0$ is sent through the scanning magnet, and the current then varies along a curve, whereby the scanning magnet scans the particle beam evenly over the surface of the product up to the time $t_1$, where the current $I_1$ is sent through the scanning magnet. The polarity of the current is rapidly turned and the product is irradiated from the other side. The negative current is increased from $I_2$ to $I_3$ according to a corresponding curve until the time $t_2$, when the cycle turns and scans back in a corresponding manner. The cycle is completed at the time $t_4$. The scanning of the current may be performed continuously or in the form of discrete steps in pace with the pulse frequency. Independently of used method, each new particle pulse will impinge on the product at a new position. In this embodiment, this step between successive particle beam pulses is about 15 mm at the product position, which means that two successive irradiation areas do overlap somewhat to ensure that all surfaces are irradiated. The total scanning width is about 400 mm, which sets the maximum width of the products to be irradiated. A total scanning cycle as described above is repeated with a frequency of 5.6 Hz. To achieve an absolutely homogeneous radiation dose over the entire surface of the product, a fine adjustment of the current profile may be performed after measurement of the radiation dose along the plane of irradiation.

In the shown embodiment, the relation between the field strength of the scanning magnet and the scanning position in very close to linear. The deviation is calculated to be maximum 3%. This does not have such a big principal importance, but may simplify the practical use. The scanning magnet has in the shown embodiment a pole gap of 4 cm. The maximum magnetic field needed in the scanning magnet is 33 mT. By a bipolar current supply of 72 V and 6 A, 174 turns are required in the magnet coils. Change of irradiation side at the lowest used field as described above performed, is in this case from +10 mT to −10 mT. This should be done as fast as possible, without making the inductive voltage too large, and in the shown embodiment, this is performed during the duration of two pulses.

The currents $I_0$ and $I_3$, respectively, thus correspond to the largest used deflection in the scanning magnet, in positive and negative direction, respectively, which in turn correspond to a radiation position in the radiation sector positioned at the end closest to the accelerator. In the same manner, the currents $I_1$, and $I_2$, respectively, correspond to a radiation position at the farther, away from the accelerator facing, end. If products with a size which do not occupy the entire width of the radiation sector are to be irradiated, the currents $I_0$, $I_1$, $I_2$, and $I_3$ may easily be adapted so as to not radiate the area outside the products. Such a control possibility of the radiation width, makes the use of the arrangement for different types of products very flexible.

The products are brought through the radiation sector in the radiation chamber on a conveyor belt, which is more closely described below. The feeding velocity is adapted so as to give the products the necessary radiation dose. Requested feeding velocity is given by the radiation power, the scanning width and the required dose and for this embodiment it is 0.76 m/min at 6 kW radiation power, 30 cm scanning width and 25 kGy dose.

The geometry of the irradiation arrangement is important. A system using directly impacting particles inevitable obtains different angle of incidence against the products since the beam is deflected from one and the same point. Either the distance between the scanning magnet and the product has to be large, or the angle of incidence will vary substantially for products of reasonable dimensions. For instance, an angle of incidence of 45 degrees against the product reduces the penetration depth by 30%. A system where all beams are redeflected before the irradiation may be constructed compact and give homogeneous angles of incidence. Furthermore, if the system is symmetric, the control of the scanning is facilitated even if this does not imply any fundamental difference.

In the irradiation arrangement, the products are normally irradiated when they are placed in a horizontal position. At use of direct impact, it is required that the accelerator arrangement is directed substantially vertically, which gives the arrangement a large height and may be impossible to install in premises with normal roof height. By using redeflected beams, one may easily create a configuration where both the accelerator device and the products may be placed substantially horizontally.

By using a relatively low particle energy, a particle accelerator of a relatively small size may be used, and the lower energy reduces the need for radiation shielding. The total size of the arrangement may, due to this and the geometrical arrangements described above, be reduced significantly and the described embodiment has a total volume of 8 $m^3$ and covers an area of 4, 2 $m^2$. The total mass is approximately 16,000 kg. This, together with the fact that the transport needs and the internal logistic problems at the irradiation arrangements are set aside by the double-sided irradiation, implies that the arrangement advantageously is used directly in a production line, which sets aside many problems in connection with transport and storage.

Figure 3:
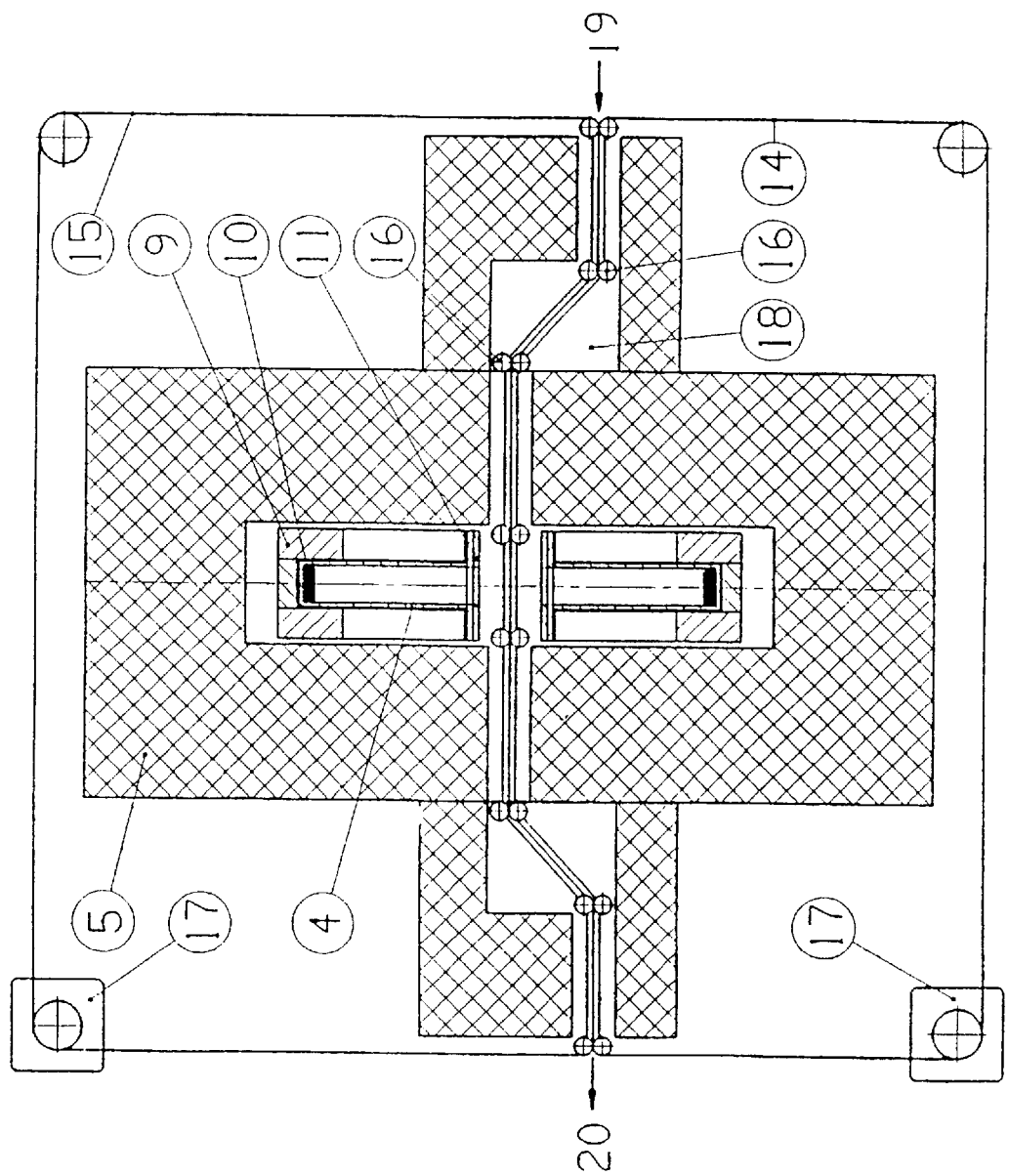
FIG. 3 is a vertical section of a sterilising device according to the present invention, taken perpendicular to the one shown in FIGS. 1 and 2, and which substantially shows the function of the conveyor belt.

In FIG. 3, a vertical section of an embodiment according to the present invention is shown, perpendicularly to the one shown in FIGS. 1 and 2, and which substantially shows the operation of the conveyor belt. The products, often in the form of tubes or other small details, packed in flabby bags, are to be transported past the particle beam with an even velocity to achieve a homogeneous radiation dose. By efficiency point of view, these products should be able to be positioned closely without risk for being moved or shadowing each other during the transport through the irradiation arrangement. This transport is performed by means of a conveyor belt, which comprises two webs 14, 15 of flexible net or the like, with a width larger than the one of the products, but which may pass through the radiation chamber 4. The products to be irradiated are transported jammed in between the two net webs. Wires or chains are arranged along the edges of the net webs, which are used to drive the net webs forward and to stay the net webs. The net webs are driven separately by one motor 17 each, but in a co-ordinated manner with each other, in a closed travelling path each. These travelling paths are connected to each other during the path at which the webs are passing through the particle radiation device, from the position 19 where the products are brought to the webs to the position 20 where the products are leaving the webs. Along this length, the wires or chains are jammed together at regular intervals by rolls 16, and in this manner the net webs jam the products to be irradiated between each other.

In order for the conveyor belt to allow for irradiation from both sides and not obstruct the particles in any substantial amount, the net of the net webs 14, 15 are made of thin metal wire, with a diameter less than 1 mm, and with a distance between the wires of approximately 20 mm. The conveyor belt is in this manner very flexible and may easily be driven along a narrow and curved tunnel by the rolls 16 through a so-called labyrinth 18. The labyrinth is necessary for stopping the secondary X-ray radiation to penetrate out from the radiation chamber. Since the products are fixed by the net webs, this passage may be performed without risk for displacements of the products along the conveyor belt. It is thus guaranteed that the velocity of the products past the radiation corresponds to the velocity of the net webs, which may be measured and regulated from the outside. This velocity is regulated to give the products the right radiation dose.

The entire irradiation device is supposed to be included in a production line and the products brought in at 19 are assumed to originate directly from a production device for the products. At the output side 20, a packaging machine may e.g. be disposed to take care of the radiation treated products.

The previous detailed description of an embodiment has only been given to facilitate the understanding of the basic idea of the invention and no additional limitations beyond what is stated by the patent claims should be understood from this, since alterations are obvious for someone skilled in the art. All numerical examples given above are tied to the specific exemplified embodiment and are not generally true for the invention as such.

Someone skilled in the art easily understands that e.g. the type of particle accelerator may be varied. The exact design of the particle extraction and acceleration is not of importance for the basic features of the invention. Given numerical examples are related to the exemplified embodiment and have generally no direct influence of the basic features of the invention, but will of course effect the design of other parts of the irradiation arrangement. The required particle energy is thus important for the design of the construction of the accelerator as well as the extent of the radiation shields. The pulse repetition frequency, the particle pulse current and the beam size effect e.g. the maximum scanning velocity.

In the same manner, it is understood that many parts of the equipment may be changed for other types with a corresponding effect. One may as one example mention that, instead of the permanent magnets used in the embodiment above, one may use electromagnets as redeflection magnets. However, these are more sensitive to radiation damages and are generally more space consuming, why permanent magnets are to prefer. However, this choice does not influence the basic feature of the invention. The scanning magnet may in a similar way also be designed in alternative ways, where the exit angle of the beam from the magnet is easily controllable.

Alternative solutions are also that the particle accelerator is designed with a controllable focusing action, or that this function is integrated with the scanning magnet. The vacuum window may in an analogue manner be designed in different ways and with different materials, but have the same basic properties, i.e. to isolate vacuum but to let the particle beam through with as small losses as possible.

The particle stopper in the described embodiment consists of a separate means disposed at the redeflection magnets. Other imaginable solutions are e.g. that they are disposed with another geometry, but still acting in the manner stated in the claims. The absorption means do not even have to consist of a separate particle stopper, but its function may e.g. be integrated in other parts of the chamber, e.g. directly in the walls of the radiation chamber.

The range of angles, within which the scanning magnet operates is of course dependent of the design of the magnet and its function, and by the geometrical configuration of the redeflection magnets and the radiation sector. Given numerical examples are related solely to the described embodiment.

It is also understood that even if the above described embodiment operates with perpendicular irradiation of the products, other geometrical configurations may be thinkable. Such changes will thereby have repercussions on the exact geometrical design of the redeflection magnets and the control of the scanning magnet. The perpendicular irradiation is, however, considered as the most favourable, since it gives the largest penetration depth for a certain particle energy for substantially planar products. For arrangements dedicated for a product with a certain geometrical shape, the optimal geometrical configuration may be different, e.g. with other irradiation directions or positioning of the radiation sector.

The details and in particular the given numerical indications of the control of the scanning magnet are also related only to the described embodiment. The same is of course valid for the design and the stated dimensions of the total size of the arrangement, which only serves to emphasize the advantage with the compact shape of the irradiation arrangement of the embodiment.

The transport system described is also solely exemplifying. The detailed design of the net webs may and should be determined by which products are to be transported. The transport webs are here described as net webs, but fully covering webs of any thin radiation durable material with low electron absorption would also be imaginable, as well as webs which only covers parts of the products.

What is claimed is:

1. In an irradiation arrangement for irradiation of products with a beam of accelerated charged particles, wherein the arrangement comprises a particle accelerator device, a radiation chamber for reception of products for irradiation comprising a radiation sector in which the irradiation of said products takes place, and a carrier device for presenting said products for irradiation from at least two sides, controllable means for scanning said beam of charged particles over the surface of said products alternately from at least two sides, said controllable means comprising:

redeflection means comprising redeflection magnets positioned at at least two sides of said radiation sector;

a controllable scanning magnet disposed to deflect respective portions of said particle beam so that each of said particle beam portions is incident toward one of said redeflection magnets; and each of said redeflection magnets has a geometrical shape which by its magnetic field deflects each incident particle beam portion from said scanning magnet towards said radiation sector in a direction substantially perpendicular to that direction the beam axis has immediately before the passage of the beam through said scanning magnet, whereby substantially the entire particle beam will pass through both the deflection in the scanning magnet and the redeflection in the redeflection magnets.

2. Irradiation arrangement according to claim 1, further comprising:

at least one absorption means for absorption of accelerated particles; and that said redeflection magnets has a geometrical shape which by its magnetic field, besides the deflection of said particle beam towards said radiation sector at the same time deflect that particle radiation which passes said radiation sector without being absorbed, towards said absorption means.

3. Irradiation arrangement according to claim 2, wherein said absorption means further includes a particle stopper, which is arranged in the space between the pole pieces of said redeflection magnets.

4. Irradiation arrangement according to claim 1, wherein each product during the irradiation is placed in the irradiation sector with the normal of the surface to be irradiated directed in a direction substantially different from the original direction of the radiation beam.

5. Irradiation arrangement according to claim 4, wherein each product during the irradiation is placed in the radiation sector with the normal of the surface to be irradiated directed substantially perpendicular to the original direction of the radiation beam.

6. Irradiation arrangement according to claim 1, wherein said controllable means also comprises a focusing lens for charged particles, whereby the focusing lens is controllable synchronous with the controllable scanning magnet to give rise to a constant beam size in the radiation sector.

7. Irradiation arrangement according to claim 1, wherein said particles are electrons.

8. Irradiation arrangement according to claim 1, wherein the particle energy used at the irradiation in the radiation sector is selected from the range 1 to 10 McV and preferably from the range 1.5 to 2.5 McV.

9. Irradiation arrangement according to claim 1, wherein said carrier device comprises a transport device which transports the products through the radiation sector, fixes the products to said transportation device during transport through said irradiation arrangement and which is connected with actuating means, whereby the actuation velocity is controllable from a position outside the radiation space.

10. Irradiation arrangement according to claim 9, wherein a predetermined radiation dose is achieved by that the actuation velocity of said carrier device through the radiation sector is controllable and dependent of the scanning width of said controllable means and the beam power of said particle acceleration device.

11. Irradiation arrangement according to claim 9, wherein the transport device comprises a conveyor belt consisting of two webs of metal wire net, connected with said actuating means, extended along the sides, and which in between fasten said products, said webs are driven, separately, but co-ordinated with each other, by respective actuating means in a closed loop each, said loops are connected to each other along at least the distance the products are transported through the irradiation arrangement, whereby said products are fixed to said transport device through jamming between said webs.

12. Irradiation arrangement for irradiation of products with a beam of accelerated charged particles and comprising a particle accelerator device, a radiation chamber for reception of products for irradiation and comprising a radiation sector, in which the irradiation of said products takes place, a carrier device for said products to be irradiated for irradiation of said products from at least two sides and controllable means for scanning of said beam of charged particles over the surface of said products alternately from at least two sides, said controllable means comprising a controllable scanning magnet for deflection of said particle beam and redeflection means, wherein said particles are electrons, which at the irradiation in said radiation sector has an energy selected from the range of 1.5 to 2.5 MeV, and wherein:

said redeflection means comprises, at at least two sides of said radiation sector, positioned redeflection magnets which are substantially circular arch shaped, said scanning magnet deflecting said particle beam so that every portion of said particle beam is incident on one of said redeflection magnets, and so that substantially all portions of said electron beam pass both the deflection in said scanning means and redeflection in said redeflection magnets and are incident to said radiation sector in a direction substantially perpendicular to the direction that the beam axis has immediately before the passage of the beam through said scanning magnet;

two particle stoppers are arranged in the space between respective pole pieces of said redeflection magnets, which particle stoppers are constituted of water cooled copper or aluminum;

the electron beam incident from said scanning magnet is deflected towards said radiation sector at the same time as the electron radiation passing said radiation sector without being absorbed, is deflected towards the particle stoppers;

said scanning magnet deflects said electron beam by an angle, the absolute value of which falls within the range of 15–45 degrees;

each product under irradiation is positioned in said radiation sector with the normal of the surface to be irradiated directed in a direction substantially perpendicular to the direction that the radiation axis has immediately before the passage of the beam through said scanning magnet;

the controllable means also comprises a focusing electron lens, which is controllable synchronously with said controllable scanning magnet to give rise to a constant beam size in said radiation sector, said carrier device comprises a conveyor belt made of two webs of metal wire net, which transports said products through said radiation sector, fixes said products to said transport device during transport through the irradiation arrangement by jamming the products between said webs and is connected with actuating means, whereby said webs are driven, separately, but in co-operation with each other, by respective actuating means in a closed loop, said loops are connected to each other along at least the distance the products are transported through the irradiation arrangement, and a predetermined radiation dose is achieved by controlling the actuation velocity of said conveyor belt from a position outside of the radiation space and is dependent on the scanning width of the controllable means and the beam power of said particle acceleration device.

13. Method for irradiating products in a radiation chamber with charged particles from a particle acceleration device by using a controllable means for scanning the beam of charged particles over the surface of said products alternately from at least two sides, whereby said method comprises the steps of:

positioning said products to be irradiated in a radiation sector;

scanning said beam of charged particles over the surface of said products alternately from at least two sides;

scanning said beam by controlling the deflection from a scanning magnet to at least one range of deflection angles and use of redeflection from at least two redeflection magnets so that every portion of said particle beam is deflected by said scanning magnet and redeflected by one of said redeflection magnets; and the positioning of each product in said radiation sector is performed in such a way that the normal of the surface to be irradiated is directed in a direction substantially different from the direction that the beam axis has immediately before the passage of the beam through said scanning magnet.

14. Method according to claim 13, wherein absorption of particles, passing the irradiation position without being absorbed, in a particle stopper.

15. Method according to claim 13, wherein said controlling of said scanning magnet comprises changing of the end points for at least one range of deflection angles, whereby requested scanning width is achieved.

16. Method according to claim 15, wherein said change in the angle range of said scanning magnet is performed such that the ranges of deflection angles, giving rise to particle paths not irradiating said products, rapidly are passed or avoided.

17. Method according to claim 13, further including focusing said particle beam with a lens for charged particles, whereby the focusing is controlled synchronously with the control of said scanning magnet so that the extension of the beam spot across the scanning direction over the irradiated product surface becomes constant.

18. Method according to claim 13, wherein the positioning of the products to be irradiated in said radiation sector and the removal of the products from said radiation sector is performed by transportation at a conveyor belt during the operation of said irradiation arrangement.

19. Method according to claim 18, further including controlling of said radiation dose by controlling the feeding velocity of said conveyor belt.

20. Method according to claim 19, wherein said controlling of the radiation dose is based on information about the power of said particle accelerating device.

21. System for production of sterile products comprising an irradiation arrangement for irradiation of products with a beam of accelerated charged particles, which irradiation arrangement comprises a particle accelerator device, a radiation chamber for reception of products for irradiation and comprising a radiation sector, in which the irradiation of said products takes place, a carrier device for presenting said products for irradiation from at least two sides and controllable means for scanning said beam of charged particles over the surface of said products alternately from at least two sides, said controllable means comprising:

redeflection means comprising redeflection magnets positioned at at least two sides of said radiation sector;

a controllable scanning magnet disposed to deflect respective portions of said particle beam so that each of said particle beam portions is incidental toward one of said redeflection magnets; and each of said redeflection magnets has a geometrical shape which by its magnetic field deflects each incident particle beam portion from said scanning magnet towards said radiation sector in a direction substantially perpendicular to that direction the beam axis has immediately before the passage of the beam through said scanning magnet.

* * * * *

UNITED STATES PATENT AND TRADEMARK OFFICE
CERTIFICATE OF CORRECTION

PATENT NO.      : 6,486,482 B1
DATED           : November 26, 2002
INVENTOR(S)     : Bengt Anderberg et al.

It is certified that error appears in the above-identified patent and that said Letters Patent is hereby corrected as shown below:

<u>Column 12,</u>
Line 63, replace "accelerating device." with -- accelerating device and the scanning width of said particle beam. --

Signed and Sealed this

Sixteenth Day of March, 2004

JON W. DUDAS
*Acting Director of the United States Patent and Trademark Office*